US007528162B2

(12) United States Patent
Kruse et al.

(10) Patent No.: US 7,528,162 B2
(45) Date of Patent: *May 5, 2009

(54) 4,5-DIHYDRO-1H-PYRAZOLE DERIVATIVES HAVING $CB_1$-ANTAGONISTIC ACTIVITY

(75) Inventors: Cornelis G. Kruse, Weesp (NL); Josephus H. M. Lange, Weesp (NL); Jacobus Tipker, Weesp (NL); Arnoldus H. J. Herremans, Weesp (NL); Herman H. Van Stuivenberg, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 338 days.

This patent is subject to a terminal disclaimer.

(21) Appl. No.: 10/490,291

(22) PCT Filed: Sep. 17, 2002

(86) PCT No.: PCT/EP02/10433

§ 371 (c)(1),
(2), (4) Date: Mar. 22, 2004

(87) PCT Pub. No.: WO03/026647

PCT Pub. Date: Apr. 3, 2003

(65) Prior Publication Data

US 2004/0248944 A1    Dec. 9, 2004

(30) Foreign Application Priority Data

Sep. 21, 2001  (EP) .................................. 01203850

(51) Int. Cl.
*A61K 31/415*  (2006.01)
*C07D 401/12*  (2006.01)

(52) U.S. Cl. ................. 514/403; 514/227.8; 514/235.5; 514/326; 544/60; 544/132; 546/211; 548/364.4; 548/365.4; 548/379.4; 548/379.7

(58) Field of Classification Search ............... 514/227.8, 514/235.5, 326, 403; 544/60, 132; 546/211; 548/364.4, 365.4, 379.4, 379.7

See application file for complete search history.

(56) References Cited

U.S. PATENT DOCUMENTS

| 4,070,365 | A |   | 1/1978  | van Daalen et al. | ...... | 548/379.4 |
| 5,292,736 | A | * | 3/1994  | Kumar et al.      | ...... | 514/231.5 |
| 5,616,601 | A |   | 4/1997  | Khanna et al.     | ...... | 514/399   |
| 5,624,941 | A |   | 4/1997  | Barth et al.      | ...... | 514/326   |
| 6,103,708 | A | * | 8/2000  | Dollings et al.   | ...... | 514/161   |
| 6,117,889 | A | * | 9/2000  | Shen et al.       | ...... | 514/339   |
| 6,476,060 | B2| * | 11/2002 | Lange et al.      | ...... | 514/403   |

FOREIGN PATENT DOCUMENTS

| WO | WO 00/46209    | 8/2000  |
| WO | WO 00/63204    | 10/2000 |
| WO | WO 01/70700 A1 | 9/2001  |
| WO | WO 03/026647 A1| 4/2003  |

OTHER PUBLICATIONS

Stella et al. "Prodrugs do thye have advantages . . ." Drugs v. 29, pp. 455-473 (1985).*
Drug.com "paxil" (2007).*
Zhou et al. "Functional magnetic stimulation . . ." EMBASE No:2005502433 (2005).*
Machiomo H. "Modulation of gastrointestinal smooth muscle . . ." FEDRIP ID:128237 (1999).*
Kruse et al. "Novel 4,5 . . ." CA 138:287664 (2003).*
Lang et al. "Novel. 3,4-diarylpyrazolines . . ." Bioorg. Med. Chem. Lett. v.15, p. 4794-4798 (2005).*
Fletcher et al. "Pyrazole . . ." CA 65:20863 (1966).*
Fathi "Pyrazole derivatives . . ." CA145:1061 (2006).*
Glombitza "Pyrazole derivatives . . ." CA 145:34218 (2006).*
Barth "Cannabionoid receptor agonists and antagonists" Exp. Op. Ther Patents 8(3):301-313 (1998).*
Thomas et al. "conformational characteristics . . ." AAPS 8(4) E665-E671 (2006).*
Patel et al. "Romonabant: . . ." Am. J. Health-sys Pharm. v.64 p. 481-489 (2007).*
Li, Z. F. et al., "Facile Synthesis of Amidines Via Intermolecular Reductive Coupling of Nitriles with Azobenzene Promoted by Samarium Diiodide", Chemical Abstracts, vol. 133:252124q, No. 18, (Oct. 30, 2000).
Pertwee, R. G., "Pharmacology Of Cannabinoid Receptor Ligands"; Current Medicinal Chemistry, vol. 6, No. 8, pp. 635-664, (1999).
Ueda, T. et al., "A Novel Ring Transformation of 5-Acylaminouracils and 5-Acylamino-Pyrimidin-4(3H)-Ones Into Imidazoles", Tetrahedron Letters, vol. 29, No. 36, pp. 4607-4610, (1988).
Kudo, N. et al., "Synthesis and Herbicidal Activity of 1,5-Diarylpyrazole Derivatives", Chem. Pharm. Bull., vol. 47, No. 6, pp. 857-868, (Jun. 1999).
Khanna, I. K. et al., "1,2-Diarylimidazoles as Potent, Cyclooxygenase-2 Selective, and Orally Active Antiinflammatory Agents", J. Med. Chem., vol. 40, No. 11, pp. 1634-1647, (1997).
Khanna, I. K. et al., "Selective Cyclooxygenase-2 Inhibitors: Heteroaryl Modified 1,2-Diarylimidzoles Are Potent, Orally Active Antiinflammatory Agents", J. Med. Chem., vol. 43, No. 16, pp. 3168-3185, (2000).
Thomas, B. F. et al., "Comparative Receptor Binding Analyses of Cannabinoid Agonists and Antagonists", The Journal of Pharmacology and Experimental Therapeutics, vol. 285, No. 1, pp. 285-292, (1998).

* cited by examiner

*Primary Examiner*—Celia Chang
(74) *Attorney, Agent, or Firm*—Finnegan, Henderson, Farabow, Garrett & Dunner, L.L.P.

(57) ABSTRACT

The present invention relates to a group of novel 4,5-dihydro-1H-pyrazole derivatives which are potent cannabinoid ($CB_1$) receptor antagonists with utility for the treatment of diseases connected with disorders of the cannabinoid system. The compounds have the general formula (I) wherein the symbols have the meanings given in the specification. The invention also relates to methods for the preparation of these compounds, and to pharmaceutical compositions containing one or more of these compounds as an active component.

16 Claims, No Drawings

4,5-DIHYDRO-1H-PYRAZOLE DERIVATIVES HAVING $CB_1$-ANTAGONISTIC ACTIVITY

This application is a National Stage application under 35 U.S.C. § 371 of PCT/EP02/10433, filed Sep. 17, 2002, which claims priority from European Patent Application EP 01203850.1, filed Sep. 21, 2001, both of which are hereby incorporated by reference.

The present invention relates to a group of novel 4,5-dihydro-1H-pyrazole derivatives, to methods for the preparation of these compounds, and to pharmaceutical compositions containing one or more of these compounds as an active component.

The above mentioned 4,5-dihydro-1H-pyrazoles are potent cannabinoid ($CB_1$) receptor antagonists with utility for the treatment of diseases connected with disorders of the cannabinoid system.

Cannabinoids are present in the Indian hemp *Cannabis sativa* and have been used as medicinal agents for centuries (Mechoulam, R. and Feigenbaum, J. J. *Prog. Med. Chem.* 1987, 24, 159). However, only within the past ten years the research in the cannabinoid area has revealed pivotal information on cannabinoid receptors and their (endogenous) agonists and antagonists. The discovery and the subsequent cloning of two different subtypes of Cannabinoid receptors ($CB_1$ and $CB_2$) stimulated the search for novel cannabinoid receptor antagonists (Munro, S. et al., *Nature* 1993, 365, 61. Matsuda, L. A. and Bonner, T. I. *Cannabinoid Receptors*, Pertwee, R. G. Ed. 1995, 117, Academic Press, London). In addition, pharmaceutical companies became interested in the development of cannabinoid drugs for the treatment of diseases connected with disorders of the cannabinoid system (Consroe, P. *Neurobiology of Disease* 1998, 5, 534. Pop, E. *Curr. Opin. In CPNS Investigational Drugs* 1999, 1, 587. Greenberg, D. A. *Drug News Perspect.* 1999, 12, 458. Pertwee, R. G., *Progress in Neurobiology* 2001, 63, 569). Hitherto, several $CB_1$ receptor antagonists are known. Sanofi disclosed their diarylpyrazole congeners as selective $CB_1$ receptor antagonists. A representative example is SR-141716A (Dutta, A. K. et al., *Med. Chem. Res.* 1994, 5, 54. Lan, R. et al., *J. Med. Chem.* 1999, 42, 769. Nakamura-Palacios, E. M. et al., *CNS Drug Rev.* 1999, 5, 43). CP-272871 is a pyrazole derivative, like SR141716A, but less potent and less $CB_1$ receptor subtype-selective than SR141716A (Meschler, J. P. et al., *Pharmacol.* 2000, 60, 1315). Aminoalkylindoles have been disclosed as $CB_1$ receptor antagonists. A representative example is Iodopravadoline (AM-630), which was introduced in 1995. AM-630 is a moderately active $CB_1$ receptor antagonist, but sometimes behaves as a weak partial agonist (Hosohata, K. et al., *Life Sc.* 1997, 61, PL115). Researchers from Eli Lilly described aryl-aroyl substituted benzofurans as selective $CB_1$ receptor antagonists (e.g. LY-320135) (Felder, C. C. et al., *J. Pharmacol. Exp. Ther.* 1998, 284, 291). 3-Alkyl-5,5'-diphenylimidazolidinediones were described as cannabinoid receptor ligands, which were indicated to be cannabinoid antagonists (Kanyonyo, M. et al., *Biorg. Med. Chem. Lett.* 1999, 9, 2233). Aventis Pharma claimed diarylmethyleneazetidine analogs as $CB_1$ receptor antagonists (Mignani, S. et al., Patent FR 2783246, 2000; *Chem. Abstr.* 2000, 132, 236982). Tricyclic pyrazoles were claimed by Sanofi-Synthelabo as $CB_1$ antagonists (Barth, F. et al., *Chem. Abstr* 2001, 134, 340504). Interestingly, many $CB_1$ receptor antagonists have been reported to behave as inverse agonists in vitro (Landsman, R. S. et al., *Eur. J. Pharmacol.* 1997, 334, R1). Reviews provide a nice overview of the cannabinoid research area (Mechoulam, R. et al., *Prog. Med. Chem.* 1998, 35, 199. Lambert, D. M. *Curr. Med. Chem.* 1999, 6, 635. Mechoulam, R. et al., *Eur. J. Pharmacol.* 1998, 359, 1. Williamson, E. M. and Evans, F. J. *Drugs* 2000, 60, 1303. Pertwee, R. G. *Addiction Biology* 2000, 5, 37. Robson, P. Br. *J. Psychiatry* 2001, 178, 107. Pertwee, R. G. *Prog. Neurobiol.* 2001, 63, 569. Goya, P; Jagerovic, N. *Exp. Opin. Ther. Patents* 2000, 10, 1529. Pertwee, R. G. *Gut* 2001, 48, 859).

It has now surprisingly been found that potent and selective antagonism of cannabinoid-$CB_1$ receptors is present in the novel 4,5-dihydro-1H-pyrazole derivatives of the formula (I), prodrugs thereof, tautomers thereof and salts thereof

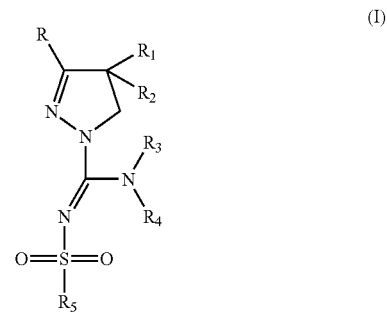

(I)

wherein
R and $R_1$ independently represent phenyl, thienyl or pyridyl which groups may be substituted with 1, 2, 3 or 4 substituents Y, which can be the same or different, from the group $C_{1-3}$-alkyl or alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R and/or $R_1$ represent naphtyl, $R_2$ represents hydrogen, hydroxy, $C_{1-3}$-alkoxy, acetyloxy or propionyloxy, $R_3$ represents a hydrogen atom or a branched or unbranched $C_{1-8}$ alkyl group or a $C_{3-7}$ cycloalkyl group which alkyl group or cycloalkyl group may be substituted with a hydroxy group, $R_4$ represents a $C_{2-10}$ branched or unbranched heteroalkyl group, $C_{3-8}$ non-aromatic heterocycloalkyl group or $C_{4-10}$ non-aromatic heterocycloalkyl-alkyl group which groups contain one or more heteroatoms from the group (O, N, S) or a $-SO_2-$ group, which $C_{2-10}$ branched or unbranched heteroalkyl group, $C_{3-8}$ non-aromatic heterocycloalkyl group or $C_{4-10}$ non-aromatic heterocycloalkyl-alkyl group may be substituted with a keto group, trifluoromethyl group, $C_{1-3}$ alkyl group, hydroxy, amino, monoalkylamino, or dialkylamino group or a fluoro atom, or $R_4$ represents an amino, hydroxy, phenoxy or benzyloxy group, or $R_4$ represents a $C_{1-8}$ alkoxy, $C_{3-8}$ alkenyl, $C_{5-8}$ cycloalkenyl or $C_{6-9}$ cycloalkenylalkyl group which groups may contain a sulphur, nitrogen or oxygen atom, a keto group or $-SO_2-$ group, which alkoxy, alkenyl and cycloalkenyl groups may be substituted with a hydroxy group, a trifluoromethyl group, an amino group, a monoalkylamino group or dialkylamino group or a fluoro atom, or $R_4$ represents a $C_{2-5}$ alkyl group which alkyl group contains a fluoro atom, or $R_4$ represents an imidazolylalkyl group, benzyl, pyridylmethyl, phenethyl or thienyl group, or $R_4$ represents a substituted phenyl, benzyl, pyridyl, thienyl, pyridylmethyl or phenethyl group wherein the aromatic rings are substituted with 1, 2 or 3 of the substituents Y, wherein Y has the meaning as indicated above, or when $R_3$ is H or methyl, $R_4$ may represent a group $NR_6R_7$ wherein

- $R_6$ and $R_7$ are the same or different and represent $C_{2-4}$ alkyl, $C_{2-4}$ trifluoroalkyl or $R_6$ represents a methyl group with the proviso that $R_7$ represents a $C_{2-4}$ alkyl group, or $R_6$ and $R_7$—together with the nitrogen atom to which they are bonded—form a saturated or unsaturated heterocyclic moiety having 4 to 8 ring atoms which heterocyclic moiety may contain an oxygen or sulphur atom or a keto group or —$SO_2$— group or an additional nitrogen atom, which saturated or unsaturated heterocyclic moiety may be substituted with a $C_{1-4}$ alkyl group, or
- $R_3$ and $R_4$ together with the nitrogen atom to which they are bonded form a saturated or unsaturated, monocyclic or bicyclic heterocyclic moiety having 4 to 10 ring atoms, which heterocyclic moiety may contain one or more atoms from the group (O, N, S) or a keto group or —$SO_2$— group, which moiety may be substituted with a $C_{1-4}$ alkyl, hydroxyalkyl, phenyl, thienyl, pyridyl, amino, monoalkylaminoalkyl, dialkylaminoalkyl, monoalkylamino, dialkylamino, aminoalkyl, azetidinyl, pyrrolidinyl, piperidinyl or hexahydro-1H-azepinyl group,
- $R_5$ represents benzyl, phenyl, thienyl or pyridyl which may be substituted with 1, 2, 3 or 4 substituents Y, wherein Y has the meaning as indicated above, which can be the same or different, or $R_5$ represents $C_{1-8}$ branched or unbranched alkyl, $C_{3-8}$ alkenyl, $C_{3-10}$ cycloalkyl, $C_{5-10}$ bicycloalkyl, $C_{6-10}$ tricycloalkyl or $C_{5-8}$ cycloalkenyl or $R_5$ represents naphtyl.

At least one centre of chirality is present (at the $C_4$ position of the 4,5-dihydro-1H-pyrazole moiety) in the compounds of the formula (I). The invention relates both to racemates, mixtures of diastereomers and the individual stereoisomers of the compounds having formula (I). Particular compounds of interest of formula (I) have the absolute stereoconfiguration at the $C_4$ position of the 4,5-dihydro-1H-pyrazole moiety as represented by formula (1ª).

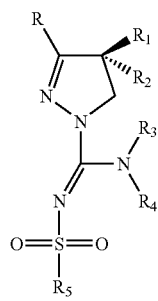

(1ª)

The invention also relates both to the E isomer, Z isomer and E/Z mixtures of compounds having formula (I).

The compounds of the invention can be brought into forms suitable for administration by means of usual processes using auxiliary substances and/or liquid or solid carrier materials.

Due to the potent $CB_1$ antagonistic activity the compounds according to the invention are suitable for use in the treatment of psychiatric disorders such as psychosis, anxiety, depression, attention deficits, memory disorders, cognitive disorders, appetite disorders, obesity, addiction, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea and cardiovascular disorders.

The affinity of the compounds of the invention for cannabinoid $CB_1$ receptors was determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand was performed by filtration over glassfiber filters. Radioactivity on the filter was measured by liquid scintillation counting.

The cannabinoid $CB_1$ antagonistic activity of compounds of the invention was determined by functional studies using CHO cells in which human cannabinoid $CB_1$ receptors are stably expressed. Adenylyl cyclase was stimulated using forskolin and measured by quantifying the amount of accumulated cyclic AMP. Concomitant activation of $CB_1$ receptors by $CB_1$ receptor agonists (e.g. CP-55,940 or (R)-WIN-55,212-2) can attenuate the forskolin-induced accumulation of cAMP in a concentration-dependent manner. This $CB_1$ receptor-mediated response can be antagonised by $CB_1$ receptor antagonists such as the compounds of the invention.

Intermediates having formula (II) (see below) can be obtained according to methods known, for example: a) Francotte, E. and Tong, Z. *Chem. Abstr.* 126, 213598; b) Rempfler, H. and Kunz, W. *Chem. Abstr.* 113, 40432; c) Rempfler, H. and Kunz, W. *Chem. Abstr.* 107, 217473.

Intermediates having formula (III) (see below), wherein $R_2$ represents hydrogen can be obtained according to methods known, for example: a) EP 0021506; b) DE 2529689; c) Grosscurt, A. C. et al., *J. Agric. Food Chem.* 1979, 27, (2), 406.

Intermediates having formula (III) (see below), wherein $R_2$ represents a hydroxy group can be obtained by reacting of a compound having formula (II)

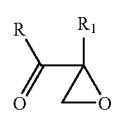

(II)

with hydrazine or hydrazine hydrate. This reaction is preferably carried out in an organic solvent, for example ethanol, and yields a compound having formula (III)

(III)

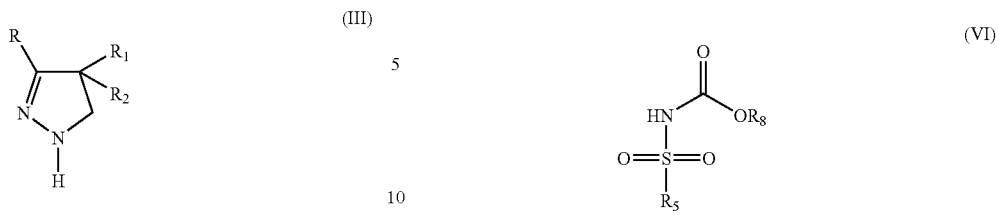

Suitable synthetic routes for the compounds of the invention are the following:

Synthetic Route A1

Step 1: reaction of a compound having formula (III) with a thioisocyanate derivative having formula (IV), (IV)

```
    NCS
    |
O=S=O
    |
    R₅
``` preferably carried out in an organic solvent, for example acetonitrile. This reaction gives a thiocarboxamide derivative having formula (V), wherein R, $R_1$, $R_2$ and $R_5$ have the meanings as described above for compound (I).

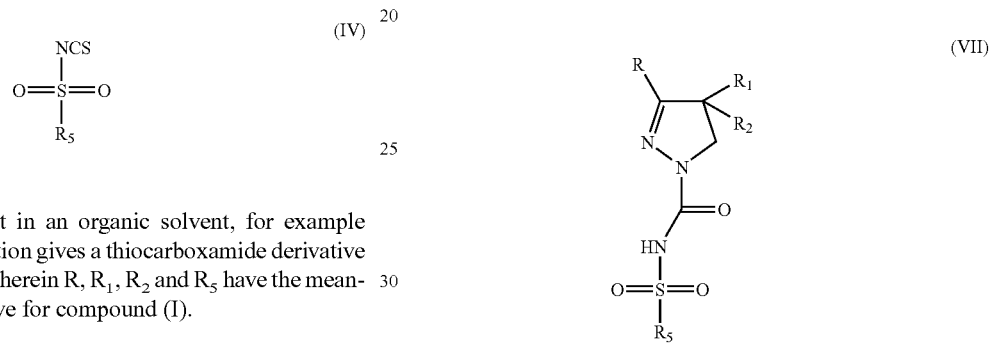

Step 2: reaction of a compound having formula (V) with a compound $R_3R_4NH$ in the presence of a mercury(II) salt, such as for example $HgCl_2$, gives a compound having formula (I). This reaction is preferably carried out in an organic solvent, such as for example acetonitrile.

Synthetic Route A2

Step 1: reaction of a compound having formula (III)

(III)

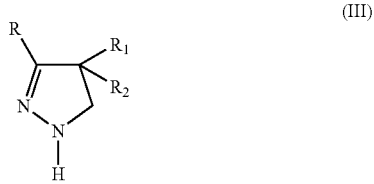

with a carbamate ester derivative having formula (VI).

(VI)

```
         O
         ||
    HN—C
         \
          OR₈
    |
O=S=O
    |
    R₅
``` wherein $R_8$ represents a lower alkyl group, for example methyl. This reaction is preferably carried out in an organic solvent, for example 1,4-dioxane, and yields a 4,5-dihydropyrazole-1-carboxamide derivative having formula (VII), wherein R, $R_1$, $R_2$ and $R_5$ have the meanings as described above for compound (I).

(VII)

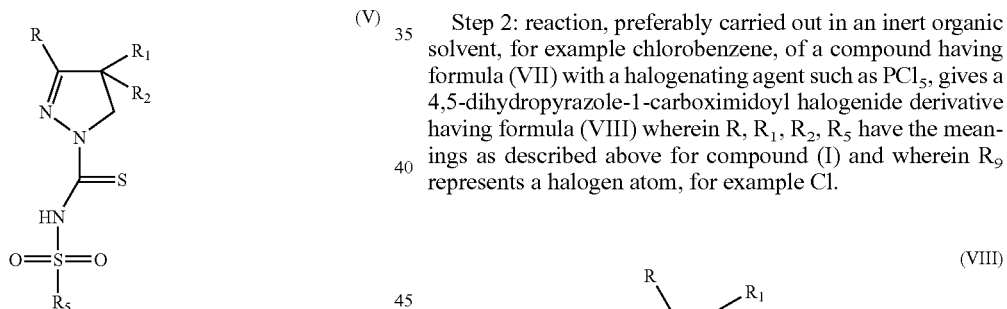

Step 2: reaction, preferably carried out in an inert organic solvent, for example chlorobenzene, of a compound having formula (VII) with a halogenating agent such as $PCl_5$, gives a 4,5-dihydropyrazole-1-carboximidoyl halogenide derivative having formula (VIII) wherein R, $R_1$, $R_2$, $R_5$ have the meanings as described above for compound (I) and wherein $R_9$ represents a halogen atom, for example Cl.

(VIII)

```
    R       R₁
     \     /
      \   / R₂
       N—N
          \
           C—R₉
           ||
           N
           |
      O=S=O
           |
           R₅
```

Step 3: reaction of a compound having formula (VIII) with a compound $R_3R_4NH$ preferably carried out in an inert organic solvent, such as for example dichloromethane gives a compound having formula (I).

Alternatively, compounds $R_3R_4NH$ which contain an additional nucleophilic nitrogen atom are reacted with a compound having formula (VIII) in such a way that the above-mentioned additional nucleophilic nitrogen atom is protected by a protective group, for example a t-butoxycarbonyl (Boc) group and the like. Subsequent removal of the protective group according to known methods yields a compound having formula (I). (See for example: T. W. Greene and P. G. M. Wuts, *"Protective Groups in Organic Synthesis"*, third edition, John Wiley & Sons, Inc., New York, 1999).

Synthetic Route A3

Step 1: reaction of a compound having formula (III)

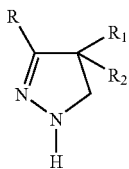

(III)

with a dithioimidocarbonic ester derivative having formula (IX).

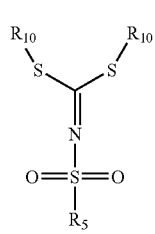

(IX)

wherein $R_{10}$ represents a $C_{1-3}$ alkyl group. This reaction is preferably carried out in an organic solvent, for example acetonitrile or toluene, and yields a carboximidothioic ester derivative having formula (X), wherein R, $R_1$, $R_2$, $R_5$ have the meanings as described above for compound (I) and wherein $R_{10}$ represents a $C_{1-3}$ alkyl group.

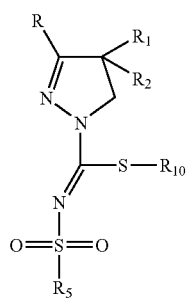

(X)

Alternatively, a compound having formula (X) can be obtained from the reaction of a compound having formula (V) with a compound $R_{10}$—X, wherein X represents a leaving group such as an iodide group, and $R_{10}$ has the meaning as described above for (X).

Step 2: Reaction, preferably carried out in an organic solvent, such as methanol, of a compound having formula (X) with a compound $R_3R_4NH$ gives a compound having formula (I).

The preparation of the compounds is illustrated in the following examples.

EXAMPLE 1

3-(4-Chlorophenyl)-N'-((4-chlorophenyl)sulfonyl)-N-(piperidin-1-yl)-4-phenyl-4,5-dihydro-1H-pyrazole-1-carboxamidine Part A: To a solution of N-((4-chlorophenyl)sulfonyl)carbamic acid methyl ester (CAS: 34543-04-9) (2.99 gram, 12.0 mmol) and pyridine (4 mL) in 1,4-dioxane (20 mL) is added 3-(4-chlorophenyl)-4-phenyl-4,5-dihydro-1H-pyrazole (3.39 gram, 13.2 mmol) and the resulting mixture is stirred for 4 hours at 100° C. After concentration in vacuo the residue is dissolved in dichloromethane, successively washed with water, 1 N HCl and water, dried over anhydrous $Na_2SO_4$, filtered and concentrated in vacuo to a volume of 20 mL. Methyl-tert-butyl ether (60 mL) is added and the resulting solution is concentrated to a volume of 20 mL. The formed crystals are collected by filtration and recrystallised from methyl-tert-butyl ether to give 3-(4-chlorophenyl)-N-((4-chlorophenyl)sulfonyl)-4-phenyl-4,5-dihydro-1H-pyrazole-1-carboxamide (4.75 gram, 76% yield) Melting point: 211-214° C.

Part B: A mixture of 3-(4-chlorophenyl)-N-((4-chlorophenyl)sulfonyl)-4-phenyl-4,5-dihydro-1H-pyrazole-1-carboxamide (1.42 gram, 3.00 mmol) and phosphorus pentachloride ($PCl_5$) (0.63 gram, 3.03 mmol) in chlorobenzene (15 mL) is heated at reflux temperature for 1 hour. After thorough concentration in vacuo, the formed 3-(4-chlorophenyl)-N-((4-chlorophenyl)sulfonyl)-4-phenyl-4,5-dihydro-1H-pyrazole-1-carboximidoyl chloride is suspended in dry dichloromethane (30 mL) and reacted with 1-aminopiperidine (1.08 mL, 10.0 mmol). After stirring at room temperature for 16 hours, the mixture is twice washed with water and concentrated in vacuo. The residue is crystallised from methyl-t-butyl ether (MTBE) to give pure 3-(4-chlorophenyl)-N'-((4-chlorophenyl)sulfonyl)-N-(piperidin-1-yl)-4-phenyl-4,5-dihydro-1H-pyrazole-1-carboxamidine (0.57 gram, 34% yield). Melting point (MP): 213-214° C. MS $ESI^+$: 556 ($MH^+$).

Analogous to the synthesis of example 1, in total 57 compounds having formula (XI) were prepared. Those are listed below in table 1 and list 1.

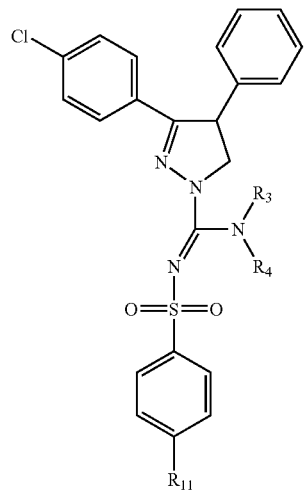

(XI)

TABLE 1

| Ex. | R$_3$ | R$_4$ | R$_{11}$ | Melting point (° C.) | MS ESI$^+$ (MH$^+$) | Salt form |
|---|---|---|---|---|---|---|
| 2 | H | Piperidin-1-yl | F | 189-190 | 540 | |
| 3 | H | Pyrrolidin-1-yl | Cl | 190-195 | 542 | |
| 4 | H | Pyrrolidin-1-yl | F | | 526 | |
| 5 | H | azepan-1-yl | Cl | 197-199 | | |
| 6 | H | Cis/trans-2,6-dimethylpiperidin-1-yl | Cl | 110-146 | | |
| 7 | H | 2,2,2-Trifluoroethylamino | Cl | 149-151 | | |
| 8 | H | t-Butoxy | Cl | 194-196 | 545 | |
| 9 | H | 2-Propoxy | Cl | 142-145 | | |
| 10 | H | Methoxy | Cl | | 503 | |
| 11 | H | Methoxy | F | | 487 | |
| 12 | H | Morpholin-4-yl | Cl | 213-216 | | |
| 13 | H | 2-(Morpholin-4-yl)ethyl | Cl | 137-139 | | |
| 14 | H | 2-(Piperidin-1-yl)ethyl | Cl | 168-169 | | |
| 15 | H | 2-(Pyrrolidin-1-yl)ethyl | Cl | 155-157 | | |
| 16 | H | 2-(Dimethylamino)ethyl | F | | | |
| 17 | CH$_3$ | 2-(Dimethylamino)ethyl | Cl | 168-170 | | .HCl |
| 18 | H | 2-(Dimethylamino)ethyl | Cl | 63-68 | | |
| 19 | H | 2-(Methylamino)ethyl | Cl | | 530 | .HCl |
| 20 | H | 2-(Ethylamino)ethyl | Cl | | 544 | .HCl |
| 21 | H | 3-(Dimethylamino)-2-methylprop-2-yl | Cl | | 572 | |
| 22 | H | (N-Methylpyrrolidin-2-yl)methyl | Cl | 149-159 | | |
| 23 | H | (N-Methylpyrrolidin-3-yl)methyl | Cl | | 570 | |
| 24 | H | 4-(Pyrrolidin-1-yl)butyl | Cl | 128-130 | 598 | |
| 25 | H | 3-(Morpholin-4-yl)propyl | Cl | | | |
| 26 | H | 3-(Dimethylamino)propyl | Cl | 221-224 | 558 | .HCl |
| 27 | CH$_3$ | 3-(Dimethylamino)propyl | F | 93 (dec.) | 556 | .HCl |
| 28 | C$_2$H$_5$ | 2-Aminoethyl | Cl | | | |
| 29 | H | 3-(Dimethylamino)propyl | F | 105-109 | 542 | .HCl |
| 30 | H | 3-(1H-Imidazol-1-yl)propyl | Cl | | | |
| 31 | H | 2-Aminoxyethyl | Cl | | 532 | |
| 32 | H | 2-(Dimethylamino)ethoxy | Cl | 201 | 560 | |
| 33 | H | 2-(Diethylamino)ethoxy | Cl | 210 | 588 | |
| 34 | H | 2-(Methoxy)ethyl | Cl | 99-102 | | |
| 35 | CH$_3$ | 2-(Acetoxy)ethyl | Cl | 157-158 | 573 | |
| 36 | H | 2-Hydroxyethyl | F | | 501 | |
| 37 | H | 2-Hydroxyethyl | Cl | | 517 | |
| 38 | H | 2-Hydroxy-2-methylpropyl | Cl | | | |
| 39 | H | 3-Hydroxypropyl | Cl | 129-132 | | |
| 40 | CH$_3$ | Hydroxy | Cl | 208-211 | | |
| 41 | H | Methoxy | CF$_3$ | 178-180 | | |
| 42 | H | 2-Fluoroethyl | Cl | 100-103 | | |
| 43 | H | 2-Fluoroethyl | CF$_3$ | 132-134 | | |

List 1

44. 3-(4-Chlorophenyl)-N-methoxy-N'-((3-methylphenyl)sulfonyl)-4-phenyl-4,5-dihydro-1H-pyrazole-1-carboxamidine. MP: 151-152° C.

45. 3-(4-Chlorophenyl)-N-methoxy-N'-((2-methylphenyl)sulfonyl)-4-phenyl-4,5-dihydro-1H-pyrazole-1-carboxamidine. MP: 145-146° C.

46. 3-(4-Chlorophenyl)-N-methoxy-N'-((2,4,5-trifluorophenyl)sulfonyl)-4-phenyl-4,5-dihydro-1H-pyrazole-1-carboxamidine. MP: 160-162° C.

47. 3-(5-Chlorothien-2-yl)-N'-((4-chlorophenyl)sulfonyl)-N-methoxy-4-phenyl-4,5-dihydro-1H-pyrazole-1-carboxamidine. MP: 180-181° C.

48. N'-((4-Chlorophenyl)sulfonyl)-3-(4-fluorophenyl)-N-methoxy-4-phenyl-4,5-dihydro-1H-pyrazole-1-carboxamidine. MP: 201-203° C.

49. 3-(4-Chlorophenyl)-N'-((4-chlorophenyl)sulfonyl)-N-methoxy-4-(3-(trifluoromethyl)phenyl)-4,5-dihydro-1H-pyrazole-1-carboxamidine.MP: 80-83° C.

50. 3-(4-Chlorophenyl)-N'-((4-chlorophenyl)sulfonyl)-N-methoxy-4-(2,6-difluorophenyl)-4,5-dihydro-1H-pyrazole-1-carboxamidine.MP: 174-177° C.

51. 3-(4-Chlorophenyl)-N'-((4-chlorophenyl)sulfonyl)-N-(2-fluoroethyl)-4-(2,6-difluorophenyl)-4,5-dihydro-1H-pyrazole-1-carboxamidine. MP: 153-155° C.

52. 3-(4-Chlorophenyl)-N'-((4-chlorophenyl)sulfonyl)-N-(2-fluoroethyl)-4-(3-fluorophenyl)-4,5-dihydro-1H-pyrazole-1-carboxamidine. MP: 130° C.

53. 3-(4-Chlorophenyl)-N-(2-fluoroethyl)-4-(3-fluorophenyl)-N'-((4-(trifluoromethyl)phenyl)sulfonyl)-4,5-dihydro-1H-pyrazole-1-carboxamidine. MP: 155° C.

54. 3-(4-Chlorophenyl)-N'-((4-chlorophenyl)sulfonyl)-4-(3-fluorophenyl)-N-(methoxy)-4,5-dihydro-1H-pyrazole-1-carboxamidine. Amorphous.

55. 3-(4-Chlorophenyl)-4-(3-fluorophenyl)-N-(methoxy)-N'-((4-(trifluoromethyl)phenyl)sulfonyl)-4,5-dihydro-1H-pyrazole-1-carboxamidine. MP: >260° C.

56. 3-(4-Chlorophenyl)-N'-((4-chlorophenyl)sulfonyl)-4-(2-fluorophenyl)-N-(methoxy)-4,5-dihydro-1H-pyrazole-1-carboxamidine. MP: 162-164° C.

57. 3-(4-Chlorophenyl)-4-(2-fluorophenyl)-N-(methoxy)-N'-((4-(trifluoromethyl)phenyl)sulfonyl)-4,5-dihydro-1H-pyrazole-1-carboxamidine. MP: 147-149° C.

In an analogous manner 29 compounds having formula (XII) were prepared. Those are listed below in table 2 and list 2.

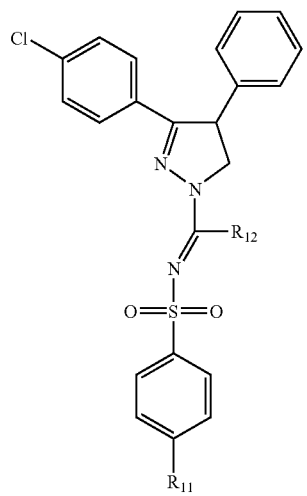

(XII)

List 2

86. N-[(3-(4-chlorophenyl)-4-(3-(trifluoromethyl)phenyl)-4,5-dihydro-1H-pyrazol-1-yl)(4-methylpiperazin-1-yl)methylene]-4-chlorobenzenesulfonamide. MP: 97-100° C.

In an analogous manner the compounds having formula (XIII) have been prepared. Those are listed in table 3 or detailed below:

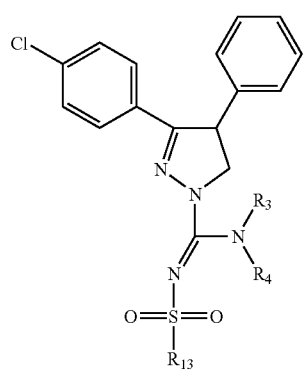

(XIII)

TABLE 2

| Ex. | $R_{11}$ | $R_{12}$ | Melting point (° C.) | MS ESI+ (MH+) | Salt form |
|---|---|---|---|---|---|
| 58 | Cl | 1,2,3,4-Tetrahydroisoquinolin-2-yl | | 589 | |
| 59 | F | 1,2,3,4-Tetrahydroisoquinolin-2-yl | | 573 | |
| 60 | F | Pyrrolidin-1-yl | | 511 | |
| 61 | Cl | Morpholin-4-yl | | 543 | |
| 62 | F | Morpholin-4-yl | | 527 | |
| 63 | Cl | Azetidin-1-yl | 200-202 | 513 | |
| 64 | F | Azetidin-1-yl | | 497 | |
| 65 | Cl | 4-Hydroxypiperidin-1-yl | 112-117 | | |
| 66 | Cl | 3-Hydroxypiperidin-1-yl | 218-222 | | |
| 67 | Cl | 4-(Hydroxymethyl)piperidin-1-yl | 185-188 | | |
| 68 | Cl | 1,1-Dioxythiomorpholin-4-yl | 120 | 591 | |
| 69 | Cl | 4-Methylpiperazin-1-yl | | 556 | |
| 70 | Cl | [1,4']-Bipiperidin-1'-yl | 260 | 624 | |
| 71 | Cl | 3,5-Cis-dimethylpiperazin-1-yl | | | |
| 72 | F | 4-Methylpiperazin-1-yl | | 540 | |
| 73 | F | 3,5-Cis-dimethylpiperazin-1-yl | | 554 | |
| 74 | F | [1,4']-Bipiperidin-1'-yl | >280 | 608 | |
| 75 | F | 4-Methyl-1,4-diazepan-1-yl | 115 | 554 | .HCl |
| 76 | Cl | 1,4-diazepan-1-yl | 84 | | |
| 77 | F | 1,4-diazepan-1-yl | | | |
| 78 | Cl | 2,6-Cis-dimethylpiperazin-1-yl | 100 (dec.) | | |
| 79 | F | 4-(Dimethylamino)piperidin-1-yl | 211-214 | | |
| 80 | F | Piperazin-1-yl | 88-90 | | |
| 81 | Cl | 4-(Pyridin-4-yl)piperazin-1-yl | 224-226 | | |
| 82 | Cl | 4-(2-Dimethylaminoethyl)piperazin-1-yl | | | |
| 83 | Cl | 4-(3-Dimethylaminopropyl)piperazin-1-yl | 163-165 | | |
| 84 | Cl | 4-(3-Hydroxypropyl)piperazin-1-yl | >140 (dec.) | | |
| 85 | Cl | 2,6-Cis-dimethyl-4-methyl piperazin-1-yl | 75-80 | | |

TABLE 3

| Example | R₃ | R₄ | R₁₃ | Melting point (° C.) | MS ESI⁺ (MH⁺) |
|---|---|---|---|---|---|
| 87 | H | 3-(Dimethylamino)propyl | CH₃ | 136-138 | |
| 88 | H | N-Methylpiperidin-4-yl | i-C₃H₇ | | |

EXAMPLE 89

N-[(4-phenyl-3-(pyridin-3-yl)-4,5-dihydro-1H-pyrazol-1-yl)(4-methylpiperazin-1-yl)methylene]-4-fluorobenzenesulfonamide Part A: 3-Pyridyl benzyl ketone (Cf. Burger et al., J. Am. Chem. Soc. 1950, 72, 1988-1990), (30.2 g, 0.153 mol) is dissolved in methanol (400 mL) and acetic acid (1.5 mL), piperidine (1.5 mL) and formaline (35 mL, 37% aqueous solution) are successively added. The resulting mixture is heated at reflux temperature for 210 minutes. The resulting mixture is allowed to attain room temperature and concentrated in vacuo. Water and 2N NaOH solution are added, followed by extraction with methyl-t-butyl ether (MTBE). The organic layer is twice washed with water, dried over Na₂SO₄, filtered and concentrated in vacuo. Flash chromatographic purification (eluant: MTBE) gives 2-phenyl-1-pyridin-3-yl propenone (21.4 gram, 67% yield) as an oil. ESI-MS (MH⁺) 210.

Part B: 2-Phenyl-1-pyridin-3-yl propenone (21.4 gram, 0.102 mol) is dissolved in ethanol (150 mL) and hydrazine hydrate is added (10.4 mL). The resulting mixture is heated at reflux temperature for 3 hours. The resulting mixture is allowed to attain room temperature and concentrated in vacuo. Water is added, followed by extraction with dichloromethane. The organic layer is washed with water, dried over Na₂SO₄, filtered and concentrated in vacuo to produce crude 4-phenyl-3-(pyridin-3-yl)-4,5-dihydro-1H-pyrazole (23 g, ~100% yield). ESI-MS (MH⁺) 224.

Part C: Crude 4-phenyl-3-(pyridin-3-yl)-4,5-dihydro-1H-pyrazole (9.81 g, 0.044 mol), [(4-chlorophenyl)sulfonyl] dithioimidocarbonic acid dimethyl ester (12.99 gram, 0.044 mol) and triethylamine (47 mL) are successively dissolved in acetonitrile. The resulting mixture is heated at reflux for 70 hours. The resulting mixture is allowed to attain room temperature and concentrated in vacuo. The residue is dissolved in dichloromethane. The organic layer is washed with water, dried over Na₂SO₄, filtered and concentrated in vacuo. Flash chromatographic purification (eluant: methanol/dichloromethane=5/95 (v/v)) gives N-((4-chlorophenyl)sulfonyl)-4-phenyl-3-(pyridin-3-yl)-4,5-dihydro-1H-pyrazole-1-carboximidothioic acid methyl ester (7.15 gram, 35% yield). ESI-MS (MH⁺) 471.

Part D: N-((4-Chlorophenyl)sulfonyl)-4-phenyl-3-(pyridin-3-yl)-4,5-dihydro-1H-pyrazole-1-carboximidothioic acid methyl ester (1.50 gram, 0.0033 mol) is suspended in toluene (25 mL) and 4-methylpiperazine (5 mL) is added. The resulting mixture is heated at 60° C. for 70 hours. The resulting yellow solution is allowed to attain room temperature and concentrated in vacuo. The resulting residue is crystallised from MTBE to give N-[(4-phenyl-3-(pyridin-3-yl)-4,5-dihydro-1H-pyrazol-1-yl)(4-methylpiperazin-1-yl)methylene]-4-fluorobenzene-sulfonamide (1.39 g, 83% yield). MP: 169-170° C.

EXAMPLE 90

(−)-(4S)-3-(4-Chlorophenyl)-N'-((4-chlorophenyl)sulfonyl)-N-methoxy-4-phenyl-4,5-dihydro-1H-pyrazole-1-carboxamidine (−)-(4S)-3-(4-Chlorophenyl)-N'-((4-chlorophenyl)sulfonyl)-N-methoxy-4-phenyl-4,5-dihydro-1H-pyrazole-1-carboxamidine ([α²⁵_D]=−165°, c=0.01, MeOH) was obtained as an amorphous solid via chiral chromatographic separation of racemic 3-(4-chlorophenyl)-N'-((4-chlorophenyl)sulfonyl)-N-methoxy-4-phenyl-4,5-dihydro-1H-pyrazole-1-carboxamidine (Chiral stationary phase: Chiralpak AD). The mobile phase consisted of ethanol.

The invention claimed is:
1. A 4,5-dihydro-1H-pyrazole compound of formula (I), a tautomer, or a stereoisomer thereof, or a hydrochloric acid salt of any of the foregoing:

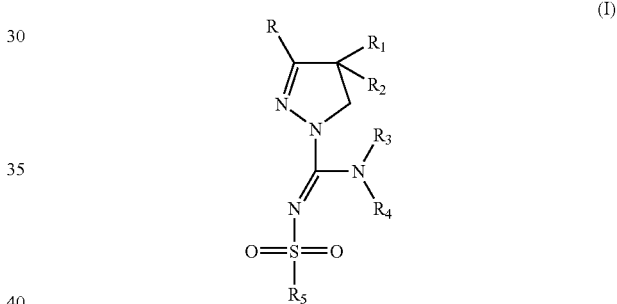

(I)

wherein:
R is chosen from a 4-chlorophenyl group, a 4-fluorophenyl group, and a 5-chlorothien-2-yl group,
R₁ is chosen from a phenyl group, a 2-fluorophenyl group, a 3-fluorophenyl group, a 3-(trifluoromethyl)phenyl group, and a 2,6-difluorophenyl group;
R₂ is a hydrogen atom;
R₃ is chosen from a hydrogen atom, a methyl group, and an ethyl group;
R₄ is a group chosen from (N-methylpyrrolidin-2-yl)methyl, (N-methylpyrrolidin-3-yl)methyl, 2-(acetoxy)ethyl, 2-(diethylamino)ethoxy, 2-(dimethylamino)ethoxy, 2-(dimethylamino)ethyl, 2-(ethylamino)ethyl, 2-(methoxy)ethyl, 2-(methylamino)ethyl, 2-(morpholin-4-yl)ethyl, 2-(piperidin-1-yl)ethyl, 2-(pyrrolidin-1-yl)ethyl, 2,2,2-trifluoro-ethylamino, 2,6-difluorophenyl, 2-aminoethyl, 2-aminoxyethyl, 2-fluoroethyl, 2-hydroxy-2-methylpropyl, 2-hydroxyethyl, 2-propoxy, 3-(1H-imidazol-1-yl)propyl, 3-(dimethylamino)-2-methylprop-2-yl, 3-(dimethylamino)propyl, 3-(morpholin-4-yl)-propyl, 3-fluorophenyl, 3-hydroxypropyl, 4-(pyrrolidin-1-yl)butyl, azepan-1-yl, cis/trans-2,6- dimethylpiperidin-1-yl, hydroxyl, methoxy, morpholin-4-yl, N-methylpiperidin-4-yl, piperidin-1-yl, pyrrolidin-1-yl, and t-butoxy, or, R₃ and R₄ together with the nitrogen atom to which they are bonded form a group chosen from [1,4']-bipiperidin-1'-yl, 1,1-dioxythiomorpholin-4-yl, 1,2,3,4-tetrahydroisoquinolin-2-yl, 1,4-diazepan-1-yl, 2,6-cis-dimethyl-4-methylpiperazin-1-yl, 2,6-cis-dimethylpiperazin-1-yl, 3,5-cis-dimethylpiperazin-1-yl, 3-hydroxypiperidin-1-yl, 4-(2-dimethylaminoethyl)piperazin-1-yl, 4-(3-dimethylaminopropyl)piperazin-1-yl, 4-(3-hydroxypropyl)piperazin-1-yl, 4-(dimethylamino)piperidin-1-yl, 4-(hydroxymethyl)-piperidin-1-yl, 4-(pyridin-4-yl)piperazin-1-yl, 4-hydroxypiperidin-1-yl, 4-methyl-1,4-diaze-pan-1-yl, 4-methylpiperazin-1-yl, azetidin-1-yl, morpholin-4-yl, and piperazin-1-yl; and R₅ is chosen from:
  benzyl, phenyl, thienyl and pyridyl groups,
    wherein the benzyl, phenyl, thienyl, and pyridyl groups are optionally substituted with 1, 2, 3 or 4 independently chosen substituents Y, which are the same or different,
    wherein Y is chosen from $C_{1-3}$-alkyl, $C_{1-3}$-alkoxy, hydroxy, halogen, trifluoromethyl, trifluoromethylthio, trifluoromethoxy, nitro, amino, mono-$(C_{1-2})$-amino, dialkyl-$(C_{1-2})$-amino, mono-$(C_{1-2})$-amido, dialkyl-$(C_{1-2})$-amido, $C_{1-3}$-alkyl sulfonyl, dimethylsulfamido, $C_{1-3}$-alkoxycarbonyl, carboxyl trifluoromethylsulfonyl, cyano, carbamoyl, sulfamoyl, and acetyl groups;
  $C_{1-8}$ branched and unbranched alkyl, $C_{3-8}$-alkenyl, $C_{3-10}$-cycloalkyl, $C_{5-10}$-bicycloalkyl, $C_{6-10}$-tricycloalkyl, and $C_{5-8}$-cycloalkenyl groups; and
  a naphthyl group.

2. The compound according to claim 1, wherein the C₄ position of the compound has an absolute stereoconfiguration of formula (Iᵃ):

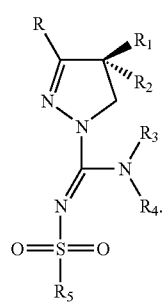

(Iᵃ)

3. The compound according to claim 1, wherein the compound of formula (I) comprises a compound of formula (XII), a tautomer, or a stereoisomer thereof, or a salt of any of the foregoing:

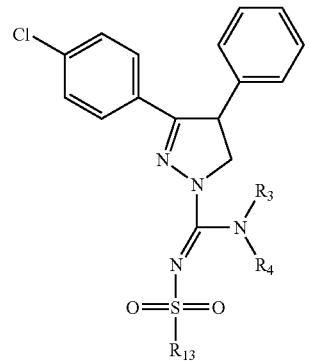

(XIII)

wherein:

| R₃ | R₄ | R₁₃ |
|---|---|---|
| H | 3-(Dimethylamino)propyl | CH₃ |
| H | N-Methylpiperidin-4-yl | i-C₃H₇ |

4. The compound according to claim 1, wherein the compound of formula (I) comprises a compound of formula (XI), a tautomer, or a stereoisomer thereof, or a salt of any of the foregoing:

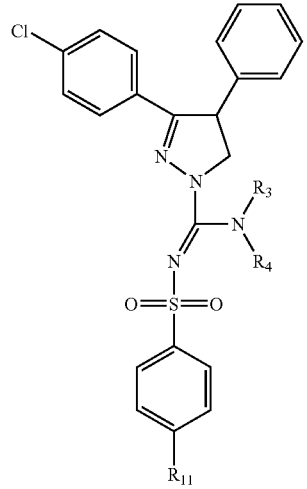

(XI)

wherein:

| R₃ | R₄ | R₁₁ |
|---|---|---|
| H | Piperidin-1-yl | Cl |
| H | Piperidin-1-yl | F |
| H | Pyrrolidin-1-yl | Cl |
| H | Pyrrolidin-1-yl | F |
| H | azepan-1-yl | Cl |
| H | Cis/trans-2,6-dimethylpiperidin-1-yl | Cl |
| H | 2,2,2-Trifluoroethylamino | Cl |
| H | t-Butoxy | Cl |
| H | 2-Propoxy | Cl |
| H | Methoxy | Cl |

-continued

| R3 | R4 | R11 |
|---|---|---|
| H | Methoxy | F |
| H | Morpholin-4-yl | Cl |
| H | 2-(Morpholin-4-yl)ethyl | Cl |
| H | 2-(Piperidin-1-yl)ethyl | Cl |
| H | 2-(Pyrrolidin-1-yl)ethyl | Cl |
| H | 2-(Dimethylamino)ethyl | F |
| CH3 | 2-(Dimethylamino)ethyl | Cl |
| H | 2-(Dimethylamino)ethyl | Cl |
| H | 2-(Methylamino)ethyl | Cl |
| H | 2-(Ethylamino)ethyl | Cl |
| H | 3-(Dimethylamino)-2-methylprop-2-yl | Cl |
| H | (N-Methylpyrrolidin-2-yl)methyl | Cl |
| H | (N-Methylpyrrolidin-3-yl)methyl | Cl |
| H | 4-(Pyrrolidin-1-yl)butyl | Cl |
| H | 3-(Morpholin-4-yl)propyl | Cl |
| H | 3-(Dimethylamino)propyl | Cl |
| CH3 | 3-(Dimethylamino)propyl | F |
| C2H5 | 2-Aminoethyl | Cl |
| H | 3-(Dimethylamino)propyl | F |
| H | 3-(1H-Imidazol-1-yl)propyl | Cl |
| H | 2-Aminoxyethyl | Cl |
| H | 2-(Dimethylamino)ethoxy | Cl |
| H | 2-(Diethylamino)ethoxy | Cl |
| H | 2-(Methoxy)ethyl | Cl |
| CH3 | 2-(Acetoxy)ethyl | Cl |
| H | 2-Hydroxyethyl | F |
| H | 2-Hydroxyethyl | Cl |
| H | 2-Hydroxy-2-methylpropyl | Cl |
| H | 3-Hydroxypropyl | Cl |
| CH3 | Hydroxy | Cl |
| H | Methoxy | CF3 |

5. The compound according to claim 1, wherein the compound of formula (I) comprises a compound of formula (XII), a tautomer, or a stereoisomer thereof, or a salt of any of the foregoing:

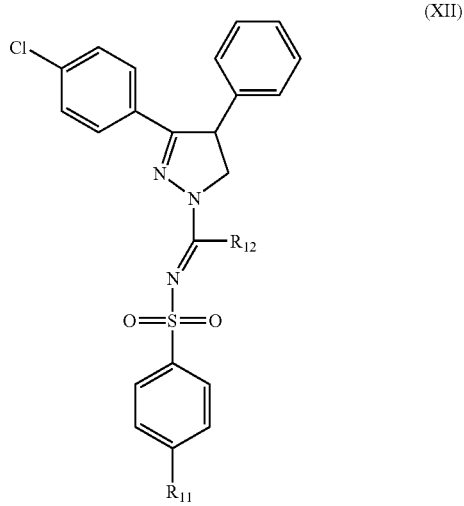

(XII)

wherein:

| R11 | R12 |
|---|---|
| Cl | 1,2,3,4-Tetrahydroisoquinolin-2-yl |
| F | 1,2,3,4-Tetrahydroisoquinolin-2-yl |
| F | Pyrrolidin-1-yl |
| Cl | Morpholin-4-yl |

-continued

| R11 | R12 |
|---|---|
| F | Morpholin-4-yl |
| Cl | Azetidin-1-yl |
| F | Azetidin-1-yl |
| Cl | 4-Hydroxypiperidin-1-yl |
| Cl | 3-Hydroxypipendin-1-yl |
| Cl | 4-(Hydroxymethyl)piperidin-1-yl |
| Cl | 1,1-Dioxythiomorpholin-4-yl |
| Cl | 4-Methylpiperazin-1-yl |
| Cl | [1,4']-Bipiperid in-1'-yl |
| Cl | 3,5-Cis-dimethylpiperazin-1-yl |
| F | 4-Methylpiperazin-1-yl |
| F | 3,5-Cis-dimethylpiperazin-1-yl |
| F | [1,4']-Bipiperid in-1'-yl |
| F | 4-Methyl-1,4-diazepan-1-yl |
| Cl | 1,4-diazepan-1-yl |
| F | 1,4-diazepan-1-yl |
| Cl | 2,6-Cis-dimethylpiperazin-1-yl |
| F | 4-(Dimethylamino)piperidin-1-yl |
| F | Piperazin-1-yl |
| Cl | 4-(Pyridin-4-yl)piperazin-1-yl |
| Cl | 4-(2-Dimethylaminoethyl)piperazin-1-yl |
| Cl | 4-(3-Dimethylaminopropyl)piperazin-1-yl |
| Cl | 4-(3-Hydroxypropyl)piperazin-1-yl |
| Cl | 2,6-Cis-dimethyl-4-methylpiperazin-1-yl. |

6. The compound according to claim 1, wherein the compound of formula (I) is chosen from:

3-(4-Chlorophenyl)-N-methoxy-N'-((3-methylphenyl)sulfonyl)-4-phenyl-4,5-dihydro-1H-pyrazole-1-carboxamidine, 3-(4-Chlorophenyl)-N-methoxy-N'-((2-methylphenyl)sulfonyl)-4-phenyl-4,5-dihydro-1H-pyrazole-1-carboxamidine, 3-(4-Chlorophenyl)-N-methoxy-N'-((2,4,5-trifluorophenyl)sulfonyl)-4-phenyl-4,5-dihydro-1H-pyrazole-1-carboxamidine, 3-(5-Chlorothien-2-yl)-N'-((4-chlorophenyl)sulfonyl)-N-methoxy-4-phenyl-4,5-dihydro-1H-pyrazole-1-carboxamidine, N'-((4-Chlorophenyl)sulfonyl)-3-(4-fluorophenyl)-N-methoxy-4-phenyl-4,5-dihydro-1H-pyrazole-1-carboxamidine, 3-(4-Chlorophenyl)-N'-((4-chlorophenyl)sulfonyl)-N-methoxy-4-(3-(trifluoromethyl)phenyl)-4,5-dihydro-1H-pyrazole-1-carboxamidine, 3-(4-Chlorophenyl)-N'-((4-chlorophenyl)sulfonyl)-N-methoxy-4-(2,6-difluorophenyl)-4,5-dihydro-1H-pyrazole-1-carboxamidine, 3-(4-Chlorophenyl)-N'-((4-chlorophenylsulfonyl)-4-(3-fluorophenyl)-N-(methoxy)-4,5-dihydro-1H-pyrazole-1-carboxamidine, 3-(4-Chlorophenyl)-4-(3-fluorophenyl)-N-(methoxy)-N'-((4-(trifluoromethyl)phenyl)sulfonyl)-4,5-dihydro-1H-pyrazole-1-carboxamidine, 3-(4-Chlorophenyl)-N'-((4-chlorophenyl)sulfonyl)-4-(2-fluorophenyl)-N-(methoxy)-4,5-dihydro-1H-pyrazole-1-carboxamidine, 3-(4-Chlorophenyl)-4-(2-fluorophenyl)-N-(methoxy)-N'-((4-(trifluoromethyl)phenyl)sulfonyl)-4,5-dihydro-1H-pyrazole-1-carboxamidine, N-[(3-(4-chlorophenyl)-4-(3-(trifluoromethyl)phenyl)-4,5-dihydro-1H-pyrazol-1-yl)(4-methylpiperazin-1-yl)methylene]-4-chlorobenzenesulfon amide, N-[(4-phenyl-3-(pyridin-3-yl)-4,5-dihydro-1H-pyrazol-1-yl)(4-methyl-piperazin-1-yl)methylene]-4-fluorobenzenesulfonamide, (−)-(4S)-3-(4-Chlorophenyl)-N'-((4-chlorophenyl)sulfonyl)-N-methoxy-4-phenyl-4,5-dihydro-1H-pyrazole-1-carboxamidine,
a tautomer or stereoisomer of any of compounds and salt of the foregoing.

7. The compound according to claim 1, wherein the compound of formula (I) comprises 3-(4-Chlorophenyl)-N'-((4-chlorophenyl)sulfonyl)-4-(3-fluorophenyl)-N-(methoxy)-4,5-dihydro-1H-pyrazole-1-carboxamidine, a tautomer, or a stereoisomer thereof, or a salt of any of the foregoing.

8. The compound according to claim 1, wherein the compound of formula (I) is chosen from 3-(4-Chlorophenyl)-N-(2-fluoroethyl)-4-(phenyl)-N'-((4-(trifluoro-methyl)phenyl)sulfonyl)-4,5-dihydro-1H-pyrazole-1-carboxamidine, and 3-(4-Chlorophenyl)-N-(2-fluoroethyl)-4-(3-fluorophenyl)-N'-((4-(trifluoro-methyl)phenyl)sulfonyl)-4,5-dihydro-1H-pyrazole-1-carboxamidine, and tautomers and stereoisomers thereof, and from salts of any of the foregoing.

9. A pharmaceutical composition comprising at least one 4,5-dihydro-1H-pyrazole compound of formula (I), at least one tautomer thereof, or at least one hydrochloric acid salt of any of the foregoing, or a mixture of any two or more of the foregoing:

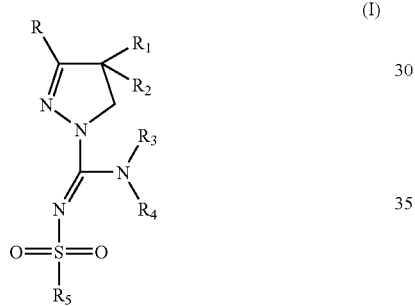

(I)

wherein:
R is chosen from a 4-chlorophenyl group, a 4-fluorophenyl group, and a 5-chlorothien-2-yl group,
$R_1$ is chosen from a phenyl group, a 2-fluorophenyl group, a 3-fluorophenyl group, a 3-(trifluoromethyl)phenyl group, and a 2,6-difluorophenyl group;
$R_2$ is a hydrogen atom;
$R_3$ is chosen from a hydrogen atom, a methyl group, and an ethyl group;
$R_4$ is a group chosen from (N-methylpyrrolidin-2-yl)methyl, (N-methylpyrrolidin-3-yl)methyl, 2-(acetoxy)ethyl, 2-(diethylamino)ethoxy, 2-(dimethylamino)ethoxy, 2-(dimethylamino)ethyl, 2-(ethylamino)ethyl, 2-(methoxy)ethyl, 2-(methylamino)ethyl, 2-(morpholin-4-yl)ethyl, 2-(piperidin-1-yl)ethyl, 2-(pyrrolidin-1-yl)ethyl, 2,2,2-trifluoro-ethylamino, 2,6-difluorophenyl, 2-aminoethyl, 2-aminoxyethyl, 2-fluoroethyl, 2-hydroxy-2-methylpropyl, 2-hydroxyethyl, 2-propoxy, 3-(1H-imidazol-1-yl)propyl, 3-(dimethylamino)-2-methylprop-2-yl, 3-(dimethylamino)propyl, 3-(morpholin-4-yl)-propyl, 3-fluorophenyl, 3-hydroxypropyl, 4-(pyrrolidin-1-yl)butyl, azepan-1-yl, cis/trans-2,6-dimethylpiperidin-1-yl, hydroxyl, methoxy, morpholin-4-yl, N-methylpiperidin-4-yl, piperidin-1-yl, pyrrolidin-1-yl, and t-butoxy, or, $R_3$ and $R_4$ together with the nitrogen atom to which they are bonded form a group chosen from [1,4']-bipiperidin-1'-yl, 1,1-dioxythiomorpholin-4-yl, 1,2,3,4-tetrahydroisoquinolin-2-yl, 1,4-diazepan-1-yl, 2,6-cis-dimethyl-4-methylpiperazin-1-yl, 2,6-cis-dimethylpiperazin-1-yl, 3,5-cis-dimethylpiperazin-1-yl, 3-hydroxypiperidin-1-yl, 4-(2-dimethylaminoethyl)piperazin-1-yl, 4-(3-dimethylaminopropyl)piperazin-1-yl, 4-(3-hydroxypropyl)piperazin-1-yl, 4-(dimethylamino)piperidin-1-yl, 4-(hydroxymethyl)-piperidin-1-yl, 4-(pyridin-4-yl)piperazin-1-yl, 4-hydroxypiperidin-1-yl, 4-methyl-1,4-diaze-pan-1-yl, 4-methylpiperazin-1-yl, azetidin-1-yl, morpholin-4-yl, and piperazin-1-yl; and $R_5$ is chosen from:
benzyl, phenyl, thienyl and pyridyl groups,
wherein the benzyl, phenyl, thienyl, and pyridyl groups are optionally substituted with 1, 2, 3 or 4 independently chosen substituents Y, which are the same or different,
wherein Y is chosen from $C_{1-3}$-alkyl, $C_{1-3}$-alkoxy, hydroxy, halogen, trifluoromethyl, trifluoromethylthio, trifluoromethoxy, nitro, amino, mono-$(C_{1-2})$-amino, dialkyl-$(C_{1-2})$-amino, mono-$(C_{1-2})$-amido, dialkyl-$(C_{1-2})$-amido, $C_{1-3}$-alkyl sulfonyl, dimethylsulfamido, $C_{1-3}$-alkoxycarbonyl, carboxyl trifluoromethylsulfonyl, cyano, carbamoyl, sulfamoyl, and acetyl groups;

$C_{1-8}$ branched and unbranched alkyl, $C_{3-8}$-alkenyl, $C_{3-10}$-cycloalkyl, $C_{5-10}$-bicycloalkyl, $C_{6-10}$-tricycloalkyl, and $C_{5-8}$-cycloalkenyl groups; and a naphthyl group;
and at least one auxiliary substance, at least one carrier material, or a combination thereof.

10. The pharmaceutical composition according to claim 9, comprising at least one 4,5-dihydro-1H-pyrazole compound of formula (I) as set forth in claim 9 in which the $C_4$ position of the compound has an absolute stereoconfiguration of formula ($I^a$):

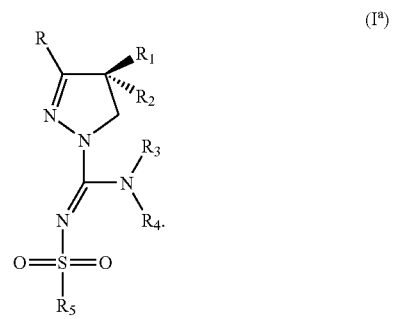

($I^a$)

11. A method of preparing a pharmaceutical composition comprising:
combining at least one 4,5-dihydro-1H-pyrazole compound of formula (I), at least one tautomer thereof, or at least one hydrochloric acid salt of any of the foregoing, or a mixture of any two or more of the foregoing:

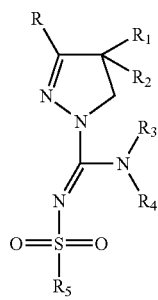

wherein:
R is chosen from a 4-chlorophenyl group, a 4-fluorophenyl group, and a 5-chlorothien-2-yl group;
$R_1$ is chosen from a phenyl group, a 2-fluorophenyl group, a 3-fluorophenyl group, a 3-(trifluoromethyl)phenyl group, and a 2,6-difluorophenyl group;
$R_2$ is a hydrogen atom;
$R_3$ is chosen from a hydrogen atom, a methyl group, and an ethyl group
$R_4$ is a group chosen from (N-methylpyrrolidin-2-yl)methyl, (N-methylpyrrolidin-3-yl)methyl, 2-(acetoxy)ethyl, 2-(diethylamino)ethoxy, 2-(dimethylamino)ethoxy, 2-(dimethylamino)ethyl, 2-(ethylamino)ethyl, 2-(methoxy)ethyl, 2-(methylamino)ethyl, 2-(morpholin-4-yl)ethyl, 2-(piperidin-1-yl)ethyl, 2-(pyrrolidin-1-yl)ethyl, 2,2,2-trifluoro-ethylamino, 2,6-difluorophenyl, 2-aminoethyl, 2-aminoxyethyl, 2-fluoroethyl, 2-hydroxy-2-methylpropyl, 2-hydroxyethyl, 2-propoxy, 3-(1H-imidazol-1-yl)propyl, 3-(dimethylamino)-2-methylprop-2-yl, 3-(dimethylamino)propyl, 3-(morpholin-4-yl)-propyl, 3-fluorophenyl, 3-hydroxypropyl, 4-(pyrrolidin-1-yl)butyl, azepan-1-yl, cis/trans-2,6-dimethylpiperidin-1-yl, hydroxyl, methoxy, morpholin-4-yl, N-methylpiperidin-4-yl, piperidin-1-yl, pyrrolidin-1-yl, and t-butoxy, or,
$R_3$ and $R_4$ together with the nitrogen atom to which they are bonded form a group chosen from [1,4']-bipiperidin-1'-yl, 1,1-dioxythiomorpholin-4-yl, 1,2,3,4-tetrahydro-isoquinolin-2-yl, 1,4-diazepan-1-yl, 2,6-cis-dimethyl-4-methylpiperazin-1-yl, 2,6-cis-dimethylpiperazin-1-yl, 3,5-cis-dimethylpiperazin-1-yl, 3-hydroxypiperidin-1-yl, 4-(2-dimethylaminoethyl)piperazin-1-yl, 4-(3-dimethylaminopropyl)piperazin-1-yl, 4-(3-hydroxypropyl)piperazin-1-yl, 4-(dimethylamino)piperidin-1-yl, 4-(hydroxymethyl)-piperidin-1-yl, 4-(pyridin-4-yl)piperazin-1-yl, 4-hydroxypiperidin-1-yl, 4-methyl-1,4-diaze-pan-1-yl, 4-methylpiperazin-1-yl, azetidin-1-yl, morpholin-4-yl, and piperazin-1-yl; and
$R_5$ is chosen from:
benzyl, phenyl, thienyl and pyridyl groups,
wherein the benzyl, phenyl, thienyl, and pyridyl groups are optionally substituted with 1, 2, 3 or 4 independently chosen substituents Y, which are the same or different,
wherein Y is chosen from $C_{1-3}$-alkyl, $C_{1-3}$-alkoxy, hydroxy, halogen, trifluoromethyl, trifluoromethylthio, trifluoromethoxy, nitro, amino, mono-$(C_{1-2})$-amino, dialkyl-$(C_{1-2})$-amino, mono-$(C_{1-2})$-amido, dialkyl-$(C_{1-2})$-amido, $C_{1-3}$-alkyl sulfonyl, dimethylsulfamido, $C_{1-3}$-alkoxycarbonyl, carboxyl trifluoromethylsulfonyl, cyano, carbamoyl, sulfamoyl, and acetyl groups;
$C_{1-8}$ branched and unbranched alkyl, $C_{3-8}$-alkenyl, $C_{3-10}$-cycloalkyl, $C_{5-10}$-bicycloalkyl, $C_{6-10}$-tricycloalkyl, and $C_{5-8}$-cycloalkenyl groups; and
a naphthyl group;
with at least one pharmacologically acceptable auxiliary substance, at least one carrier material, or a combination thereof;
wherein the at least one compound of formula (I) is present in an amount effective for treating at least one cannabinoid neurotransmission disorder, at least one disease involving cannabinoid neurotransmission, or a combination of the at least one disorder and at least one disease in a patient in need of treatment for the at least one disease, the at least one disorder, or the combination.

12. The method according to claim 11, wherein the composition comprises at least one 4,5-dihydro-1H-pyrazole compound of formula (I) as set forth in claim 11 in which the $C_4$ position of the compound has an absolute stereoconfiguration of formula ($I^a$):

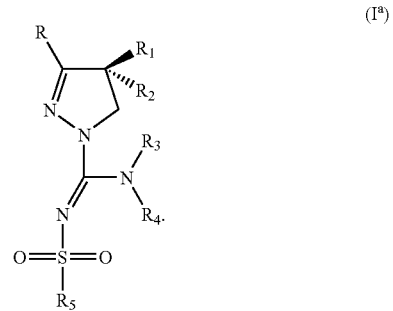

13. A method of treating a psychiatric disorder chosen from psychosis, anxiety, depression, attention deficit disorders, memory disorders, cognitive disorders, appetite disorders, obesity, addiction, appetence, and drug dependence.

14. A method of treating a neurological disorder chosen from neurodegenerative disorders, dementia, dystonia, muscle spasticity, tremor, epilepsy, multiple sclerosis, traumatic brain injury, stroke, Parkinson's disease, Alzheimer's disease, Huntington's disease, Tourette's syndrome, cerebral ischaemia, cerebral apoplexy, crainiocerebral trauma, stroke, spinal cord injury, neuroinflammatory disorders, plaque sclerosis, viral encephalitis, and demyelinisation disorders.

15. A method of treating a pain in a human or animal patient in need of such treating comprising administering to the patient a pharmaceutical composition comprising at least one 4,5-dihydro-1H-pyrazole compound of formula (I) according to claim 9, in an amount efficacious for the treating.

16. The method according to claim 15, wherein the pain is neuropathic pain.

* * * * *